United States Patent [19]

Meiss

[11] Patent Number: 5,000,746
[45] Date of Patent: Mar. 19, 1991

[54] WOUND COVERING HAVING CONNECTED DISCRETE ELEMENTS

[75] Inventor: Ludwig Meiss, Hamburg, Fed. Rep. of Germany

[73] Assignee: Friedrichsfeld GmbH Keramik- und Kunststoffwerke, Mannheim, Fed. Rep. of Germany

[21] Appl. No.: 230,826

[22] Filed: Aug. 11, 1988

[30] Foreign Application Priority Data

Aug. 11, 1987 [DE] Fed. Rep. of Germany ....... 3726617

[51] Int. Cl.$^5$ .................... A61F 13/00; A61F 15/00
[52] U.S. Cl. .................... 604/304; 128/155; 128/156; 424/443; 424/445
[58] Field of Search .............. 128/155, 90, 156; 604/304; 424/443, 445

[56] References Cited

U.S. PATENT DOCUMENTS

| | | | |
|---|---|---|---|
| 2,621,145 | 12/1952 | Sano | 128/155 |
| 3,662,405 | 5/1972 | Bortz et al. | 623/16 |
| 3,814,097 | 6/1974 | Ganderton et al. | |
| 3,842,830 | 10/1974 | Hárgest | |
| 3,905,367 | 9/1975 | Dapirch | 604/293 |
| 3,930,498 | 1/1976 | Monnet et al. | 128/889 |
| 4,018,646 | 4/1977 | Ruffo et al. | 428/245 X |
| 4,323,063 | 4/1982 | Fisichella | 128/863 |
| 4,337,186 | 6/1982 | Crisp et al. | 525/362 |
| 4,373,519 | 2/1983 | Errede et al. | 128/D21 X |
| 4,427,003 | 1/1984 | Fennimore et al. | 128/90 |
| 4,569,343 | 2/1986 | Kimura | 128/155 |
| 4,672,956 | 6/1987 | Potter et al. | 128/90 |
| 4,745,912 | 5/1988 | McMurray | 128/90 |
| 4,748,977 | 6/1988 | Guyot et al. | 128/156 |
| 4,748,978 | 6/1988 | Kamp | 128/156 |
| 4,793,336 | 12/1988 | Wang | 128/156 |

FOREIGN PATENT DOCUMENTS 1161384 1/1964 Fed. Rep. of Germany .

Primary Examiner—Randall L. Green
Assistant Examiner—Paul Prebilic
Attorney, Agent, or Firm—Foley & Lardner, Schwartz, Jeffery, Schwaab, Mack, Blumenthal & Evans

[57] ABSTRACT

A wound covering for burns, extensive skin wounds, skin lesions or the like, which are subject to contamination by germs, including fungi, and may then become slow healing septic wounds which require a special wound covering and wound treatment. The wound covering may either comprise a plurality of individual elements connected by connecting members into a network, and having, at least on the surface, a layer of ceramic or glass, or it may comprise a base, particularly a mat, web or fabric, provided with glass or ceramic layer. The wound coverings according to the invention are permeable to oxygen and liquids, biocompatible and may also be bioactive.

17 Claims, 1 Drawing Sheet

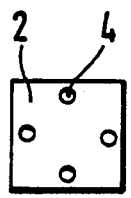
FIG.1
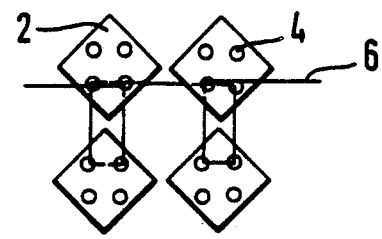
FIG.2
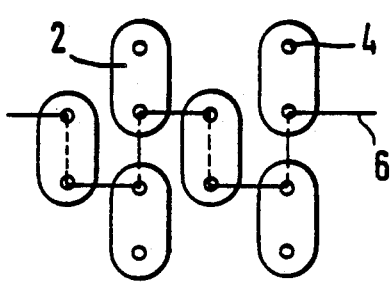
FIG.3
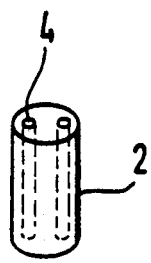
FIG.4
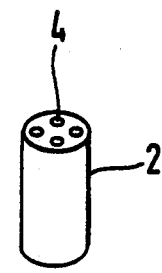
FIG.5
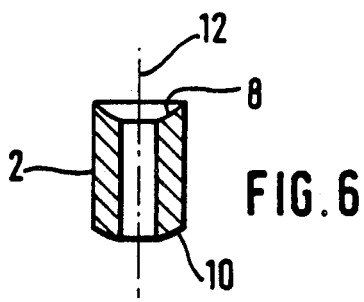
FIG.6
FIG.8
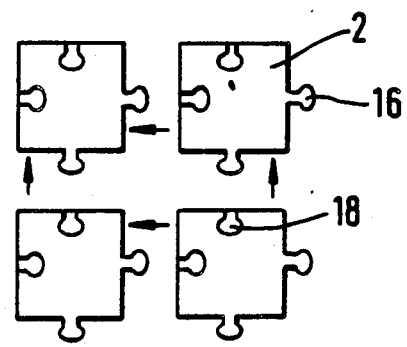
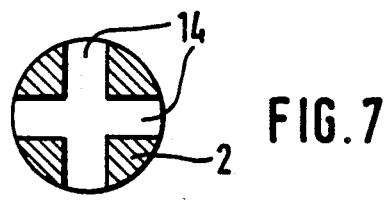
FIG.7

WOUND COVERING HAVING CONNECTED DISCRETE ELEMENTS

BACKGROUND OF THE INVENTION

Wound coverings are, as is known, required for burns, extensive skin wounds or skin lesions, open soft tissue injuries, pressure sores (decubitus), leg ulcers (ulcera cruris), wound ruptures (wound dehiscences) and the like. Wounds of this type are subject to contamination by germs (including fungi) and may then become septic wounds, which are slow to heal and require a special wound covering and wound treatment.

For such applications there exist to date gauze compresses and compresses of other suitable materials, whereby organic materials, in particular pigskin or collagen web, or metal foils such as, in particular, aluminum foils are employed. Moreover, synthetic organic materials can be used in the form of foams, gels or films, mats and powders. These include adipose gauze, polyurethane foams and mats, coverings of polytetrafluoride or polyvinyl chloride, Teflon/polyurethane foils, silicone-based materials and liquid-absorbing powders (e.g. based on dextran). The presently known wound coverings made from such materials are usually applied to the wounds in the form of sheets or mats. Wound exudate may thereby occasionally be retained under the covering material which is used, and this may subsequently lead to a delay in healing of the wound. If bacterial invasion occurs, a festering infection results, even in some cases when the dressing is changed several times a day.

West German Auslegeschrift DE-AS No. 1,161,384 discloses a metallized, absorbent dressing material. This dressing material comprises a fine-pored, absorbent, felt-like, compacted fiber fleece which is provided with a fine metal coating on the fiber surfaces without impairing the web structure. Metallized dressing materials of this type do not convey any impetus to provide a layer of ceramic or glass in the sense of the present invention in order to achieve the advantages and effects described hereinafter.

Further, U.S. Pat. No. 3,842,830 discloses a material for the formation of a surgical dressing which consists of inert ceramic microparticles and a method for forming such a dressing in situ. These microparticles have a specific weight of over 1 and, in addition, are of a size in the range of mesh number 100 to 3000. This previously known surgical dressing is produced on the spot by applying the aforementioned ceramic microparticles directly onto the wet tissue surfaces in the area of the injury. The microparticles can be dusted like powder onto the wound. A connection by means of connecting members or a web is the opposite of this previously known formation of a surgical dressing in situ.

The principal requirement for such wound coverings is for permeability to oxygen and liquids (e.g. wound exudates and therapeutic solutions). Moreover, such coverings should be made tissue-compatible and should promote granulation, i.e. they should be biocompatible and also, if possible, bioactive. An additional requirement is for sufficient mechanical flexibility. The aforementioned requirements are not met in a satisfactory manner with the previously known materials since, as a rule, only individual requirements are satisfied, and not all requirements simultaneously.

SUMMARY OF THE INVENTION

It is the object of the present invention to provide an improved wound covering which avoids the disadvantages of prior art wound coverings.

It is also an object of the present invention to provide a wound covering which is pervious to oxygen as well as wound exudates and/or therapeutic solutions, and which is compatible with living tissues, promotes granulation, and exhibits satisfactory mechanical stability.

These and other objects of the invention are achieved by providing a wound covering formed from a permeable web comprising ceramic or glass at least at the surface. The web may comprise a plurality of individual elements either made of or coated with ceramic or glass and connected by means of connecting members into a network, or it may comprise a permeable base web provided with a layer of ceramic or glass.

The proposed wound covering ensures a satisfactory contact with the wound base as a result of its tissue compatibility and the possibility for exudate to pass therethrough, in particular germ-containing exudate, i.e. pus. Healing can be reliably improved by means of the wound covering, and an improved initial condition is created for the event of a skin graft. Surprisingly, as a result of the type of surface proposed according to the invention, whether made up of elements connected to form a network or of a coated base, the formation of clean granulation tissue is promoted. It has been found that when a wound covering according to the invention is used, the intervals between changes of dressings can be significantly extended in comparison with previously disclosed wound coverings. The elements connected to form a network have, like the coated base, a good flexibility and can be fitted without any difficulty to the contour of the wound to be covered.

According to the invention, the elements are provided at least on their surface, with a layer of ceramic or glass, it being possible within the scope of the invention for the elements to be produced entirely from the ceramic or glass. The elements can be provided with holes or continuous bores for producing the network, whereby a one-dimensional or multi-dimensional network is built up by means of threads passed therethrough. The elements can be connected by means of special connecting members or methods to form a one-dimensional or multidimensional network, whereby their size and shape is designed according to the requirements. The connecting members can also be formed directly on the elements and can, in the form of hooks and eyelets, grooves and tongues, snap closures or in a similar manner, effect the mutual connection of the individual elements.

In the alternative embodiment a resilient, flexible base, which is constructed in particular as a mat, web or fabric, is provided with a layer of ceramic or glass. Such bases may consist of metal, ceramic or of an organic web. The coating can be produced reliably and in a simple manner using known techniques, it being possible, in this context, to employ in particular thermal spraying processes, electrophoresis, CVD (chemical vapor deposition) processes and PVD (plasma vapor deposition) processes.

The proposed wound covering satisfies, in a single unitary form device, the above-mentioned requirements and has outstanding permeability to oxygen and liquids. It is tissue-compatible, promotes granulation and is distinguished by a good mechanical flexibility.

It should be expressly noted at this point that the wound covering need not be composed of identical, individually corresponding elements. Rather, within the scope of the invention, bodies of varying geometry and size may be utilized in each case for a wound covering. The elements can be constructed as plates or sheets, tubes, spheres or even as rings which cover only a fraction of the wound area to be covered. As used herein, the term "projected area" refers to the area blocked off by the elements viewed perpendicularly to the plane of the covering. Due to the presence of spaces between the elements, the projected area is normally only a fraction of the area of the covering.

The bodies or elements may be liquid impermeable or they may be porous, and they can suitably be made of a bioinert material, such as aluminum oxide ($Al_2O_3$). Alternatively, the bodies or elements may comprise a bioactive material such as a calcium phosphate, preferably tricalcium phosphate, or hydroxy apatite. The bodies or elements may also be formed of bioglass or bioglass ceramic materials. According to one preferred embodiment the bodies can be provided with antibiotics and/or antiseptic (antibacterial, antiviral, antimycotic) substances.

The connecting members may be formed of any suitable organic thread material.

Finally, within the scope of the invention, the elements or the material itself used for the coating, and the connecting members or the base can also have an antiseptic action. It has been found that silver compounds have such an action, and thus, in particular the ceramic which is used, can be treated according to the invention with such a silver compound, e.g. by wetting the material with a solution of an antiseptic silver compound.

BRIEF DESCRIPTION OF THE DRAWINGS

The invention will be explained in further detail hereinafter with reference to illustrative preferred embodiments shown in the accompanying drawings in which:

FIG. 1 shows an individual square-shaped element;

FIG. 2 shows a partial view of a wound covering of several square elements according to FIG. 1;

FIG. 3 shows part of a wound covering with oblong elements;

FIGS. 4 and 5 show cylindrical elements with two and four bores respectively, through which threads may be passed;

FIG. 6 shows a longitudinal section through a cylindrical element with rounded end faces;

FIG. 7 shows a section through a spherical element; and

FIG. 8 shows elements with interlocking hooks and eyelets.

DETAILED DESCRIPTION OF PREFERRED EMBODIMENTS

FIG. 1 shows a small square element 2, at approximately two to five times its natural size. The element 2 could also have another outer contour, for example it could be rectangular, rhomboid, round or the like in form. The thickness of this element 2, i.e. viewed perpendicularly to the plane of the drawing, is about one to several millimeters. This element 2 has four bores 4 through which one or even more threads are passed in order to produce the connection with other corresponding elements.

FIG. 2 shows a plan view of part of a wound covering which is put together from a plurality of square elements 2 to form a network. In order to connect these plate-like elements 2, a thread 6 is provided which is threaded as shown in the drawing through the bores 4 of elements 2 adjacent to each other. It can be seen that the connection to the other plate-like elements 2 can be made using other threads in a corresponding manner. The essential feature is that, using the connecting members which here consist by way of example of threads, a plurality of small elements 2 are connected to each other, whereby the elements have a layer of ceramic or glass at least on the surface. Of course, the elements can also consist entirely of such a material.

FIG. 3 shows, again only partially, a wound covering whose elements 2 now have an elongate or oval form. These elements 2 are also substantially plate-like in form, whereby the material thickness lies in the millimeter range. In order to effect the mutual connection, these elements 2 each have two bores 4 through which threads can be passed.

FIGS. 4 and 5 show embodiments of elements which are constructed in substantially cylindrical form and have two and four longitudinal bores 4, respectively. Such cylindrical elements 2 can be connected to each other by means of threads in the manner of a chain, one behind the other in axial direction; a plurality of such "chains" are arranged alongside each other and together form the wound covering.

FIG. 6 shows an advantageous embodiment of the again cylindrically shaped element 2. As can be seen in this longitudinal axial sectional view, the upper end face 8 is designed concave and the lower end face 10 is designed convex. Such elements 2 are arranged one behind the other in the direction of the longitudinal axis 12, the convex end faces being accordingly received in the concave end faces of adjacent elements. Here too, a plurality of such "chains" can be provided alongside each other without any problems, by means of connecting members in the form of threads or the like.

FIG. 7 shows a further embodiment of the element, which in this case is constructed spherical in form. As can be seen, two bores 14 are provided which are orthogonal to each other and through which, in a corresponding manner, connecting members in the form of threads can be passed in order to produce a complete wound covering.

FIG. 8 shows an embodiment in which elements 2 have interlocking hooks and eyelets or lugs and ears 16 and 18. The sheets 2, which are of essentially square design, have, on two longitudinal sides, two such hooks 16 and, on the two other sides, two eyelets 18, in the manner shown. The hooks and eyelets can be designed in the form of snap closures so that, with simple production, a reliable connection is nevertheless assured. In order to ensure a good flexibility and mobility of the individual elements 2 with respect to each other, the hooks 16 are of (semi)spherical design and are inserted with slight play into the similarly rounded eyelets.

The foregoing description and examples have been set forth merely to illustrate the invention and are not intended to be exclusive. Since modifications of the foregoing embodiments incorporating the spirit and substance of the invention may occur to persons skilled in the art, the scope of the invention should be limited solely with reference to the appended claims and equivalents.

What is claimed is:

1. A wound covering comprising a permeable web which remains flexible during use with a surface of ceramic or glass, wherein said permeable web comprises a plurality of individual elements each having a surface of ceramic or glass, and said elements have the form of plates, sheets, tubes, spheres or rings and are joined together by connecting members to form a network.

2. A wound covering as claimed in claim 1, wherein said individual elements are composed entirely of ceramic or glass.

3. A wound covering as claimed in claim 1, wherein said individual elements are provided with only a surface layer of ceramic or glass.

4. A wound covering as claimed in claim 1, wherein said surface of each element is comprised of bioinert material.

5. A wound covering as claimed in claim 4, wherein said bioinert material is aluminum oxide.

6. A wound covering as claimed in claim 1, wherein said elements are comprised of a bioactive material.

7. A wound covering as claimed in claim 1, wherein said elements are comprised of bioinert and bioactive materials.

8. A wound covering as claimed in claim 3, wherein said elements are comprised of a nonceramic core surrounded by an outer layer of ceramic or glass.

9. A wound covering as claimed in claim 1, wherein said permeable web is formed of inorganic material.

10. A wound covering as claimed in claim 1, wherein said connecting members are comprised of an organic material.

11. A wound covering as claimed in claim 1, wherein said elements are spaced apart such that said wound covering covers an overall area which is greater than the sum of individual areas covered by said individual elements.

12. A wound covering as claimed in claim 6, wherein said bioactive material is selected from the group consisting of calcium phosphates, hydroxy apatite, bioglass and bioceramic.

13. A wound covering as claimed in claim 12, wherein said bioactive material is tricalcium phosphate.

14. A wound covering as claimed in claim 1, wherein said elements are porous.

15. A wound covering as claimed in claim 1, wherein said elements are treated with an antibiotic or antiseptic substance selected from the group consisting of antibacterial agents, antiviral agents and antimycotic agents.

16. A wound covering, comprising a permeable web which remains flexible during use, said web comprising a plurality of individual elements each having a surface of ceramic or glass and joined together by connecting members to form a network, wherein said wound covering is comprised of a material having an antiseptic action.

17. A wound covering as claimed in claim 16, wherein said material having antiseptic action is impregnated with a silver compound, whereby said silver compound causes said material to exert antiseptic action.

* * * * *